(12) United States Patent
Amin (10) Patent No.: US 11,965,151 B2
(45) Date of Patent: Apr. 23, 2024

(54) SELF-CONTAINED BIOLOGICAL INDICATOR

(71) Applicant: ASP Global Manufacturing GmbH, Schaffhausen (CH)

(72) Inventor: Behnam Amin, Mission Viejo, CA (US)

(73) Assignee: ASP Global Manufacturing GMBH (CH)

( * ) Notice: Subject to any disclaimer, the term of this patent is extended or adjusted under 35 U.S.C. 154(b) by 451 days.

(21) Appl. No.: 17/155,970

(22) Filed: Jan. 22, 2021

(65) Prior Publication Data

US 2021/0147784 A1 May 20, 2021

Related U.S. Application Data (62) Division of application No. 15/057,768, filed on Mar. 1, 2016, now Pat. No. 10,907,126.

(51) Int. Cl.
*A61L 2/28* (2006.01)
*C12M 1/12* (2006.01)
*C12Q 1/22* (2006.01)

(52) U.S. Cl.
CPC ............... *C12M 37/06* (2013.01); *A61L 2/28* (2013.01); *C12Q 1/22* (2013.01)

(58) Field of Classification Search
CPC . C12M 37/06; C12M 1/34; A61L 2/28; C12Q 1/22; C12Q 1/04
See application file for complete search history.

(56) References Cited

U.S. PATENT DOCUMENTS

| | | |
|---|---|---|
| 2,447,988 A | 8/1948 | Pierson |
| 3,346,464 A | 10/1967 | Ernst |
| 3,450,319 A | 6/1969 | Ray et al. |
| 3,752,743 A | 8/1973 | Henshilwood |
| 3,948,727 A | 4/1976 | Steiger |
| 4,291,122 A | 9/1981 | Orelski |
| 4,304,869 A | 12/1981 | Dyke |

(Continued)

FOREIGN PATENT DOCUMENTS

| | | |
|---|---|---|
| CA | 738687 A | 7/1966 |
| CA | 823163 A | 9/1969 |

(Continued)

OTHER PUBLICATIONS

US 8,945,737 B2, 02/2015, Franciskovich et al. (withdrawn)
(Continued)

*Primary Examiner* — Liban M Hassan
(74) *Attorney, Agent, or Firm* — Lerner David LLP (57) ABSTRACT

A biological sterilization indicator is disclosed that in some embodiments comprises a housing having a first enclosure and a second enclosure, an ampule containing a liquid growth medium, and an insert disposed at least partially in the first enclosure. The insert may have a platform including a top surface, an abutment surface, and a side surface, as well as a first void disposed in the platform and configured to allow passage of a first volume of the liquid growth medium into the second enclosure and a second void disposed through at least a portion of the side surface and configured to allow passage of a second volume of the liquid growth medium into the second enclosure. Methods of using the indicator are also disclosed.

8 Claims, 7 Drawing Sheets

(56) References Cited

U.S. PATENT DOCUMENTS

| | | |
|---|---|---|
| 4,528,268 A | 7/1985 | Andersen et al. |
| 4,537,099 A | 8/1985 | Oster et al. |
| 4,546,086 A | 10/1985 | Hounsell |
| 4,637,139 A | 1/1987 | Chen |
| 4,717,661 A | 1/1988 | McCormick et al. |
| 4,732,850 A | 3/1988 | Brown et al. |
| 4,741,437 A | 5/1988 | Gorski et al. |
| 4,839,291 A | 6/1989 | Welsh et al. |
| 4,883,641 A | 11/1989 | Wicks et al. |
| 4,885,253 A | 12/1989 | Kralovic |
| 5,028,543 A | 7/1991 | Finch et al. |
| 5,073,488 A | 12/1991 | Matner et al. |
| 5,167,923 A | 12/1992 | Van Iperen |
| 5,223,401 A | 6/1993 | Foltz et al. |
| 5,252,484 A | 10/1993 | Matner et al. |
| 5,293,816 A | 3/1994 | Musumeci, Sr. et al. |
| 5,362,654 A | 11/1994 | Pouletty |
| 5,405,580 A | 4/1995 | Palmer |
| 5,415,994 A | 5/1995 | Imrich et al. |
| 5,418,167 A | 5/1995 | Matner et al. |
| 5,482,171 A | 1/1996 | Palmer |
| 5,516,648 A | 5/1996 | Malchesky et al. |
| 5,552,320 A | 9/1996 | Smith |
| 5,736,355 A | 4/1998 | Dyke et al. |
| 5,739,004 A | 4/1998 | Woodson |
| 5,750,184 A | 5/1998 | Imburgia |
| 5,759,848 A | 6/1998 | Nagoshi et al. |
| 5,770,393 A | 6/1998 | Damasso et al. |
| 5,801,010 A | 9/1998 | Falkowski et al. |
| 5,830,683 A | 11/1998 | Henricks et al. |
| 5,863,790 A | 1/1999 | Bolea |
| 5,866,356 A | 2/1999 | Albert et al. |
| 5,942,438 A | 8/1999 | Antonoplos et al. |
| 6,218,189 B1 | 4/2001 | Antonoplos et al. |
| 6,436,659 B1 | 8/2002 | Hui et al. |
| 6,458,554 B1 | 10/2002 | Hui et al. |
| 6,551,555 B2 | 4/2003 | Antonoplos et al. |
| 6,924,139 B2 | 8/2005 | Eveland et al. |
| 7,091,042 B2 | 8/2006 | Lemus et al. |
| 7,247,482 B2 | 7/2007 | Lemus et al. |
| 7,642,067 B2 | 1/2010 | Song et al. |
| 8,173,388 B2 | 5/2012 | Pasmore et al. |
| 8,173,418 B2 | 5/2012 | Sestak et al. |
| 8,173,438 B1 | 5/2012 | Putnam et al. |
| 8,765,398 B2 | 7/2014 | Dalmasso |
| 8,840,837 B2 | 9/2014 | Smith et al. |
| 8,915,413 B2 | 12/2014 | Kayser |
| 8,945,837 B2 | 2/2015 | Franciskovich et al. |
| 8,969,029 B2 | 3/2015 | Chandrapati et al. |
| 8,980,622 B2 | 3/2015 | Smith |
| 9,145,573 B2 | 9/2015 | Pederson et al. |
| 9,321,973 B2 | 4/2016 | Marchand et al. |
| 9,322,046 B2 | 4/2016 | Chandrapati et al. |
| 9,525,317 B2 | 12/2016 | Ohashi et al. |
| 9,675,722 B2 | 6/2017 | Ahimou et al. |
| 9,856,124 B2 | 1/2018 | Mitidieri |
| 10,059,977 B2 | 8/2018 | Witcher et al. |
| 10,150,901 B2 | 12/2018 | Boutier et al. |
| 10,561,753 B2 | 2/2020 | Thompson et al. |
| 2004/0197848 A1 | 10/2004 | Behun et al. |
| 2005/0014214 A1 | 1/2005 | Eveland et al. |
| 2008/0070272 A1 | 3/2008 | Franciskovich et al. |
| 2009/0068716 A1 | 3/2009 | Hirota et al. |
| 2011/0200992 A1 | 8/2011 | Chandrapati et al. |
| 2012/0149094 A1 | 6/2012 | Smith et al. |
| 2012/0156090 A1 | 6/2012 | Dane et al. |
| 2013/0210048 A1 | 8/2013 | Chandrapati et al. |
| 2013/0217107 A1 | 8/2013 | Pederson et al. |
| 2013/0224849 A1 | 8/2013 | Chandrapati et al. |
| 2013/0273594 A1 | 10/2013 | Ahimou et al. |
| 2015/0004682 A1 | 1/2015 | Smith et al. |
| 2015/0167047 A1 | 6/2015 | Smith et al. |
| 2015/0337354 A1 | 11/2015 | Ahimou et al. |
| 2016/0000954 A1 | 1/2016 | Ahimou et al. |
| 2017/0175071 A1 | 6/2017 | Sullivan et al. |
| 2017/0211035 A1 | 7/2017 | Yirava et al. |
| 2017/0253845 A1 | 9/2017 | Behnam |
| 2018/0015193 A1 | 1/2018 | Swaminathan et al. |
| 2018/0071421 A1 | 3/2018 | Fang et al. |
| 2018/0187142 A1 | 7/2018 | Troung |
| 2018/0237821 A1 | 8/2018 | Fryer |
| 2019/0002951 A1 | 1/2019 | Fryer et al. |
| 2019/0106725 A1 | 4/2019 | Cregger et al. |
| 2019/0106726 A1 | 4/2019 | Cregger et al. |
| 2019/0169672 A1 | 6/2019 | Fryer et al. |
| 2020/0165658 A1 | 5/2020 | Bala et al. |

FOREIGN PATENT DOCUMENTS

| | | |
|---|---|---|
| CA | 1 182 729 A | 2/1985 |
| CN | 1853734 A | 11/2006 |
| CN | 201453688 U | 5/2010 |
| CN | 102596261 A | 7/2012 |
| CN | 203307339 U | 11/2013 |
| CN | 105087361 A | 11/2015 |
| CN | 204814967 U | 12/2015 |
| CN | 105561362 A | 5/2016 |
| CN | 106267277 A | 1/2017 |
| CN | 106966348 A | 7/2017 |
| CN | 206473580 U | 9/2017 |
| CN | 206970617 U | 2/2018 |
| EP | 0 152 298 A2 | 8/1985 |
| EP | 1032822 B1 | 5/2003 |
| EP | 2968634 B1 | 12/2016 |
| FR | 2708287 B1 | 10/1995 |
| GB | 1055387 A | 1/1967 |
| IN | 201747012748 A | 4/2017 |
| IN | 201714046902 A | 7/2018 |
| JP | H10201466 A | 8/1998 |
| JP | H11196893 A | 7/1999 |
| JP | 2017123976 A | 7/2017 |
| JP | 2018201397 A | 12/2018 |
| RU | 129814 U1 | 7/2013 |
| RU | 143648 U1 | 7/2014 |
| RU | 146719 U1 | 10/2014 |
| RU | 2683644 C2 | 4/2019 |
| WO | 92/19764 A1 | 11/1992 |
| WO | 97/35189 A1 | 9/1997 |
| WO | 00/50634 A1 | 8/2000 |
| WO | 2005/036128 A2 | 4/2005 |
| WO | 2008/106327 A2 | 9/2008 |
| WO | 2010/039388 A2 | 4/2010 |
| WO | 2010/045138 A2 | 4/2010 |
| WO | 2016/057520 A1 | 4/2016 |
| WO | 2016/205953 A1 | 12/2016 |
| WO | 2018/025207 A1 | 2/2018 |
| WO | 2018/160449 A1 | 9/2018 |
| WO | 2020/136463 A1 | 7/2020 |
| WO | 2021/053627 A1 | 3/2021 |

OTHER PUBLICATIONS

Russian Search Report for Registration No. 2017145872/04(078515) dated Dec. 26, 2017, Date of valid search completion: Jun. 10, 2021, 2 pages.

PCT Notification of Transmittal of the International Search Report and the Written Opinion of the International Searching Authority, or the Declartion for International Application No. PCT/IB2021/060235, dated Feb. 18, 2022, 9 Pages.

Namsa, Self-Contained Biological Indicators for Monitoring Steam, Northwood, Ohio, 2015.

Anonymous, 3M™ Attest™ 1292E Rapid Readout Biological Indicator, Internet Article, Jan. 1, 1999, http://multimedia.3m.com/mws/mediawebserver?mwsId=SSSSSu7zK1fslxtU48_el8mGev7qe17zHvTSevTSeSSSSSS--&fn=Rapid_Readout_Profile_1292E.pdf.

Chinese First Office Action and Search Report for Chinese Patent Application No. 201810004516.1 dated Aug. 3, 2020 and English translation.

PCT Notification of Transmittal of the International Search Report and the Written Opinion of the International Searching Authority, or (56) References Cited

OTHER PUBLICATIONS the Declaration for International Application No. PCT/IB2020/058750 dated Nov. 27, 2020, 1 page.
PCT Written Opinion of the International Searching Authority for International Application No. PCT/IB2020/058750 dated Nov. 27, 2020, 6 pages.
PCT International Search Report for International Application No. PCT/IB2020/058750 dated Nov. 27, 2020, 6 pages.

SELF-CONTAINED BIOLOGICAL INDICATOR

CROSS-REFERENCE TO CO-PENDING APPLICATION

The present application is a Divisional Application under 35 U.S.C. § 121 of U.S. patent application Ser. No. 15/057,768, filed Mar. 1, 2016. The entire contents of this application is incorporated by reference herein in its entirety.

FIELD

The subject matter disclosed herein relates to self-contained biological sterilization indicators.

BACKGROUND

Medical devices are typically sterilized before use in order to minimize the likelihood that a contaminated device might be used on a subject, which could cause an infection in the subject. Various sterilization techniques may be employed, such as steam, hydrogen peroxide, and vapor phase sterilization, either with or without a gas plasma and ethylene oxide (EtO). Each of these methods depends to a certain extent on the diffusion rates of the sterilization fluids, typically gases, upon the medical devices to be sterilized.

Before sterilization, medical devices are typically packaged within containers or pouches having a semi-permeable barrier that allows transmission of the sterilizing fluid—sometimes referred to as a sterilant—but prevents admission of contaminating organisms, particularly post-sterilization and until the package is opened by medical personnel. For the sterilization cycle to be efficacious, the contaminating organisms within the package must be killed because any organisms that survive the sterilization cycle could multiply and re-contaminate the medical device.

Although the packaging helps prevent contamination of a sterile medical device, the packaging may increase the difficulty of achieving a successful sterilization cycle because the packaging impedes the sterilant from reaching the device or instrument contained therein. This is particularly problematic for devices and instruments that have diffusion-restricted spaces therein because these diffusion-restricted spaces reduce the likelihood that a sterilization cycle may be effective. For example, endoscopes typically have long narrow lumens into which the sterilant must diffuse in sufficient concentration for sufficient time to achieve a successful sterilization cycle.

Confirming that a sterilization cycle has been efficacious helps medical personnel avoid using a contaminated medical device on a subject. Typically, the sterilized medical device is not itself checked for contaminating organisms because such an activity would introduce other contaminating organisms to the medical device, thereby re-contaminating it. Thus, an indirect check has been developed in the form of a sterilization indicator.

A sterilization indicator is a device that may be placed alongside or in proximity to a medical device being subject to a sterilization cycle, such that the sterilization indicator is subject to the same sterilization cycle as the medical device. For instance, a biological indictor having a predetermined quantity of microorganisms possessing known resistance to the sterilant may be placed into a sterilization chamber alongside a medical device and subjected to a sterilization cycle. After the cycle is complete, the microorganisms in the biological indicator may be cultured to determine whether any of the microorganisms survived the cycle.

Certain biological indicators are referred to as being "self-contained." These biological indicators typically include a housing that contains a quantity of microorganisms and a source of growth media in a frangible container that is located near the microorganisms. Like other biological indicators, the "self-contained" biological indicator ("SCBI") may be subject to a sterilization cycle alongside medical devices. Following the cycle, the frangible container may be broken to release the growth media and culture any surviving microorganisms in situ. The SCBI may be incubated at elevated temperatures, typically around 50° C. to 60° C., which encourages outgrowth of the surviving microorganisms. Incubation using commercially available products typically lasts for about twenty-four hours. During this time, while the effectiveness of the sterilization remains unconfirmed, it is desirable that medical personnel do not use the medical devices. This may cause inventory management inefficiencies for a health care provider, such as a hospital, because, for example, the medical devices should be stored while they cannot be used, perhaps requiring the health care provider to keep more medical devices in its inventory than it otherwise would to ensure a sufficient supply of medical devices. Alternatively, health care providers may use the medical devices before the incubation is completed and sterilization efficacy confirmed. However, using the medical devices before sterilization efficacy has been confirmed may expose a subject of a medical procedure to risk of infection from the medical devices.

After incubation, the SCBI is analyzed to detect the presence of microorganisms. Should any microorganisms be detected, the sterilization cycle may be considered to have been ineffective. Should no microorganisms be detected, the sterilization cycle may be considered to have been effective. Some SCBIs are designed to incorporate a growth medium that changes color in the presence of microorganisms. This color change may be due to a shift in pH that occurs due to acid production by live microorganisms that metabolize a growth medium, which also contains a pH indicating dye. Other SCBIs are designed to incorporate a growth medium that includes a fluorophore whose fluorescence depends on the amount of viable microorganisms contained in the medium. For these SCBIs, a color change or change in the amount of fluorescence indicates that surviving microorganisms may have multiplied during incubation.

The frangible container of the SCBI that contains the liquid growth medium is often fabricated from glass. The glass must be sufficiently robust to avoid breakage during transportation, e.g., from the manufacturer of the SCBI to a health care provider. Such robustness, however, corresponds to a greater force required to break the ampule at the desired time by medical personnel. Accordingly, some SCBI manufacturers provide activation devices to hospital personnel to assist them in breaking the ampule.

The microorganisms of the SCBI are often placed on a carrier. The carrier may be fabricated from various materials such as paper or glass fibers. The carrier may become damaged, particularly during transportation, if the components within the SCBI, such as the frangible container, are not restrained from contacting the carrier. For example, during transportation, the frangible container may jostle within the SCBI, which may cause the frangible container to repeatedly batter the carrier and damage it. Such damage may increase the likelihood that the carrier may become dislodged from a position in which it should be disposed for proper functioning of the SCBI.

A color change or turbidity change in the liquid growth medium of an SCBI may be determined visually by individual health-care personnel, without the assistance of automated equipment. Alternatively, a color change, turbidity change, or a fluorescence change may be determined by the assistance of automated equipment incorporating color and/or fluorescence sensors. The accuracy of such determinations may be diminished by the presence of broken pieces of what was once the frangible container that contained the growth medium because these pieces may block or partially occlude the optical path between the SCBI and the sensor, or they may change the wavelength of light or the amount of fluorescence from the SCBI that the sensor may detect. Furthermore, the broken pieces may prevent the full amount of a required volume of growth medium from contacting the carrier because they may contact the carrier, thereby providing an obstruction between the growth medium and the carrier. The broken pieces may also create small volumes therebetween that contain, e.g., air, gases, and vapors that may need to be displaced for a sufficient quantity of the growth medium to reach the carrier.

SUMMARY

A biological sterilization indicator is disclosed that in some embodiments comprises a housing having a first enclosure and a second enclosure, an ampule containing a liquid growth medium, and an insert disposed at least partially in the first enclosure. In some embodiments, a portion of the ampule is disposed inside the first enclosure and no portion of the ampule being disposed inside the second enclosure. In some embodiments, the insert has a platform including a top surface, an abutment surface, and a side surface. In some embodiments, the insert has a first void disposed in the platform and configured to allow passage of a first volume of the liquid growth medium into the second enclosure. In some embodiments, the insert has a second void disposed through at least a portion of the side surface and configured to allow passage of a second volume of the liquid growth medium into the second enclosure. In some embodiments, the second void of the insert may be an angled cut through the abutment surface and the side surface. In some embodiments, the angled cut may be disposed entirely beneath the top surface. In some embodiments, the insert further includes a wall disposed on the top surface of the platform. In some embodiments the wall has a cylindrical form.

A biological sterilization indicator, particularly one configured in accordance with at least some of the embodiments described in the preceding paragraph, may be used to perform a method that includes the steps of providing the biological sterilization indicator, breaking the ampule, allowing passage of the first volume of the liquid growth medium through the first void, and allowing passage of the second volume of the liquid growth medium through the second void. The method may further include the step of inhibiting a liquid lock from forming.

A biological sterilization indicator is disclosed that in some other embodiments comprises a housing, an ampule, a cap, a carrier, and an insert. In some of these embodiments the housing has an inner side wall, an inner bottom wall, a first enclosure, a second enclosure, and a support in the inner side wall, wherein the first enclosure is disposed above the support, and the second enclosure is disposed between the inner bottom wall and the support. In some of these embodiments the ampule has a first end and a second end, and at least a portion of the ampule is disposed inside the first enclosure. In some of these embodiments the cap has an inner surface and an outer surface, and the cap is disposed on a portion of the housing that includes at least a portion of the first enclosure. In some of these embodiments, the carrier is disposed on the inner bottom wall. In some of these embodiments the insert has a platform, which includes a top surface and an abutment surface. In some of these embodiments the second end of the ampule is disposed on the top surface and the abutment surface is disposed on the support. In some of these embodiments the insert has a leg that extends toward the inner bottom wall. In some of these embodiments the leg has a length that is less than the distance between the support and the inner bottom wall such that there is a clearance between the carrier and leg. In some of these embodiments the length of the leg is between approximately 0.1 and 2 millimeters less than the distance between the support and the inner bottom wall. In some of these embodiments the top surface of the platform includes at least three stress concentrators and the second end of the ampule contacts each of the at least three stress concentrators. In some of these embodiments the ampule is disposed within an annular projection originating on the inner surface of the cap, which extends toward the second enclosure of the housing. In some of these embodiments the first end of the ampule is coupled to the annular projection by a friction fit. In some of these embodiments the ampule has an annular cross section with an outer diameter that is between approximately 0.1 and 1 millimeters less than an inner diameter of the annular projection. In some of these embodiments the inner surface of the cap contacts the first end of the ampule.

A biological sterilization indicator is disclosed that in still other embodiments comprises a housing, an ampule, a cap, and an insert. In some of these embodiments, the housing has a first enclosure, a second enclosure, and a first wall including a support disposed between the first enclosure and the second enclosure. In some of these embodiments, the ampule has a first end and a second end, and at least a portion of the ampule is disposed inside the first enclosure. In some of these embodiments, the cap is disposed on a portion of the housing that includes at least a portion of the first enclosure, and the cap has an inner surface and an outer surface. In some of these embodiments, the cap has an insert having a platform, which is disposed upon the support. In some of these embodiments, the insert has a first stress concentrator, a second stress concentrator, and a third stress concentrator. In some of these embodiments, each stress concentrator is disposed on the platform and each contacts the second end of the ampule. In some of these embodiments, the insert further includes a second wall originating on the platform and extending away from the second enclosure.

In further embodiments of the still other embodiments in which the biological sterilization indicator includes at least a first stress concentrator, a second stress concentrator, and a third stress concentrator, each stress concentrator has a triangular form that includes a base portion, a height portion, and a hypotenuse portion. In some of these embodiments, each base portion contacts the platform, each height portion contacts the second wall, and each hypotenuse portion contacts the second end of the ampule. In some of these embodiments, the angle between the platform and the hypotenuse portion of the first stress concentrator is different than the angle between the platform and the hypotenuse portion of the second stress concentrator. In some of these embodiments the angle between the platform and the hypotenuse portion of the first stress concentrator is different than the angle between the platform and the hypotenuse portion of the third stress concentrator, and the angle between the platform and the hypotenuse portion of the second stress concentrator is different than the angle between the platform and the hypotenuse portion of the third stress concentrator. In some of these embodiments the angle between the platform and the hypotenuse portion of the second stress concentrator is within approximately five degrees of the angle between the platform and the hypotenuse portion of the third stress concentrator. In some of these embodiments, the angle between the platform and the hypotenuse portion of the second stress concentrator is equal to the angle between the platform and the hypotenuse portion of the third stress concentrator.

In further embodiments of the still other embodiments in which the insert further includes a second wall originating on the platform and extending away from the second enclosure, the cap is moveable from a first position to a second position. In some of these embodiments the cap includes a projection originating at the inner surface of the cap and extending toward the insert. In some of these embodiments the cap includes an arm that originates at the second wall and extends toward the cap such that the arm is adapted to impede movement of the cap via interference with the projection. In some of these embodiments the arm is adapted to move from a first orientation to a second orientation to allow movement of the cap to the second position. In some of these embodiments, the arm includes an aperture therethrough. In some of these embodiments the projection is adapted to move from a third orientation to a fourth orientation. In some of these embodiments the arm is positioned relative to the projection such that the ampule is positioned to impede flexion of the projection from the third orientation to the fourth orientation. In some of these embodiments the arm is positioned relative to the projection such that the ampule is positioned to impede flexion of the arm from the first orientation to the second orientation.

A biological sterilization indicator, particularly one configured in accordance with at least some of the embodiments described in the two preceding paragraphs, may be used to perform a method that includes the steps of exerting an applied force on the biological sterilization indicator and generating at least five reaction forces at discrete locations on the ampule.

As used herein, the term "surface" should be understood as a feature of an object that forms a boundary of the object.

As used herein, the term "wall" should be understood as a feature of an object that forms at least a portion of a side, top, or bottom, of that object. A wall is an example of a surface.

As used herein, the term "abutment surface" should be understood as a surface of an object that contacts another object.

As used herein, the term "enclosure" should be understood as a space or cavity inside an object that is at least partially defined by surfaces of that object or surfaces of other objects contained therein.

As used herein, the term "insert" should be understood as an object that is disposed within one or more enclosures of an object.

As used herein, the term "void" should be understood as a feature of an object that is devoid of solid material and that is bounded by at least a portion of one surface or wall of the object. A void may provide a passage through an object. A void may be used to maintain fluid communication through or around the object.

As used herein, the term "liquid lock" should be understood as a blockage in the path of a volume of flowing liquid, the blockage being formed at least in part by a volume of a stationary gas and/or liquid.

As used herein, the term "inhibit" should be understood as reducing the likelihood that an undesired result, such as formation of a liquid lock, occurs.

As used herein, the term "cut" should be understood as a type of void that has been made or that resembles having been made by removing material from an object. Examples of cuts include features such as chamfers and bevels.

As used herein, the term "support" should be understood as a feature that helps maintain the position of another feature or object.

As used herein, the term "leg" should be understood as an elongate member of an object that originates at and extends away from another feature of that object.

As used herein, the term "carrier" should be understood as an object upon which microorganisms and/or enzymes have been disposed.

As used herein, the term "applied force" should be understood as a force exerted by a user directly or indirectly to an object, with or without the assistance of another object or device.

As used herein, the term "reaction force" should be understood as a force generated by an object subject to an applied force in response to the applied force, where at least a component of the reaction force points in a direction opposite to the direction of the applied force.

As used herein, the term "stress concentrator" should be understood as a feature that includes a surface area configured to exert a reaction force against an object subject to an applied force, exerted directly or indirectly on the object, where the surface area configured to exert a reaction force is less than a surface area of the object upon which the applied force is exerted.

As used herein, the term "projection" should be understood as a feature of an object that originates at and extends away from a surface of that object.

As used herein, the term "annular" should be understood as indicating that a feature has a cross section that is at least partially elliptical and/or circular.

As used herein, the term "friction fit" should be understood as a coupled relationship between two or more surfaces that is achieved by friction.

As used herein, the term "arm" should be understood as an elongate member of an object that originates at and extends away from another feature of that object.

As used herein, the term "impede" should be understood as causing at least a partial or temporary obstruction of movement.

As used herein, the term "flex" should be understood as a bending action that occurs in a bendable object or feature caused by application of a deflective force to the object or feature.

As used herein, the term "orientation" should be understood as an angular attitude of an object or feature.

The biological sterilization indicator disclosed herein is sufficiently robust to survive transportation without ampule breakage or carrier degradation while reducing the amount of force required to break the ampule by depressing the cap. The biological sterilization indicator disclosed herein prevents artifacts, such as pieces of a broken glass ampule, from entering the second enclosure of the housing, which helps to prevent such artifacts from introducing error into a measurement of the color or fluorescence of the growth medium. The biological sterilization indicator disclosed herein helps to avoid formation of blockages among such artifacts that could impede a desired quantity of the growth medium from contacting the carrier.

BRIEF DESCRIPTION OF THE DRAWINGS

While the specification concludes with claims which particularly point out and distinctly claim the subject matter described herein, it is believed the subject matter will be better understood from the following description of certain examples taken in conjunction with the accompanying drawings, in which like reference numerals identify the same elements and in which:

DETAILED DESCRIPTION

The following description sets forth certain illustrative examples of the claimed subject matter. Other examples, features, aspects, embodiments, and advantages of the technology should become apparent to those skilled in the art from the following description. Accordingly, the drawings and descriptions should be regarded as illustrative in nature.

I. A Self-Contained Biological Indicator

Figure 1:
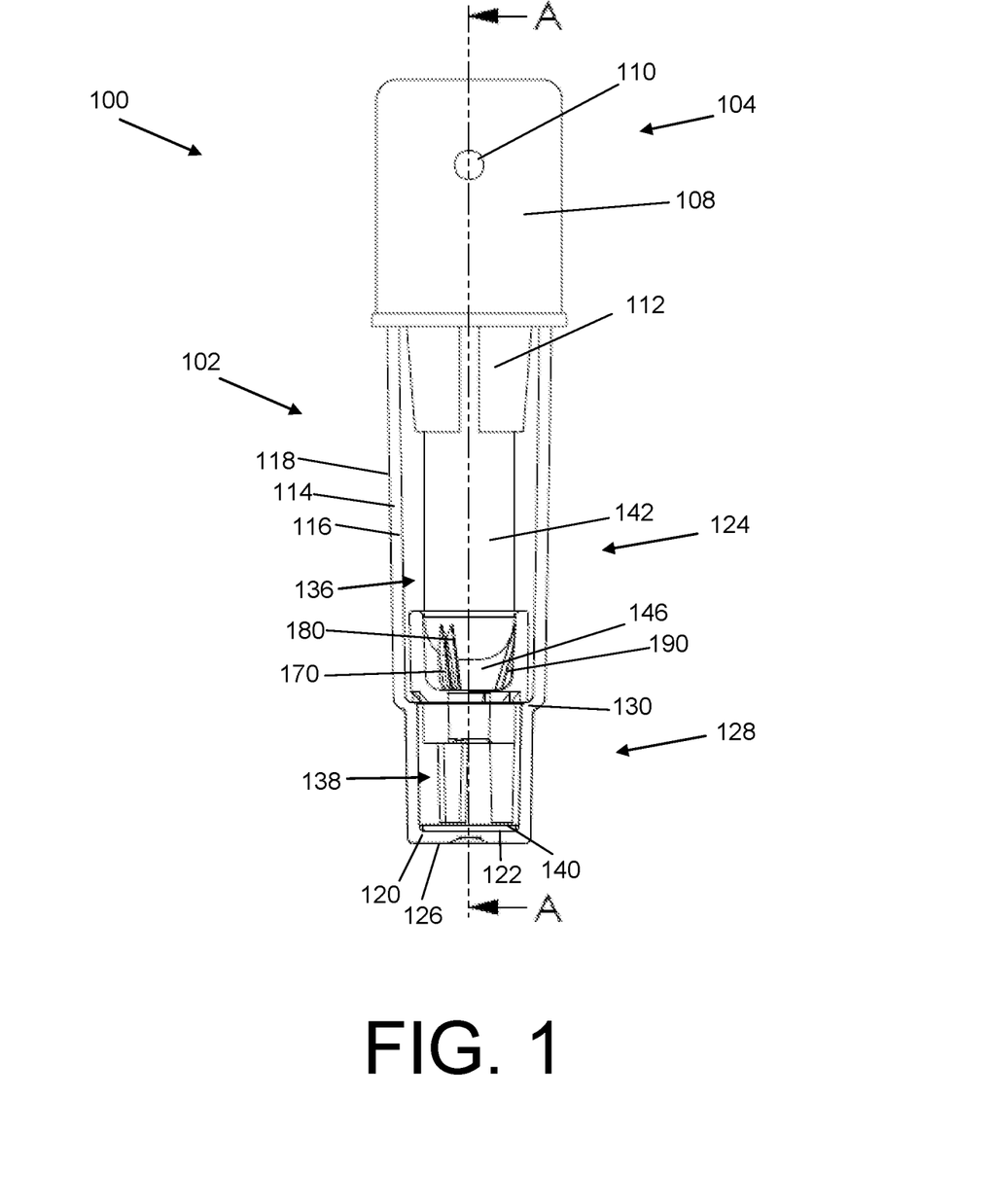
FIG. 1 depicts a side view of a first example embodiment of an SCBI.
Figure 2:
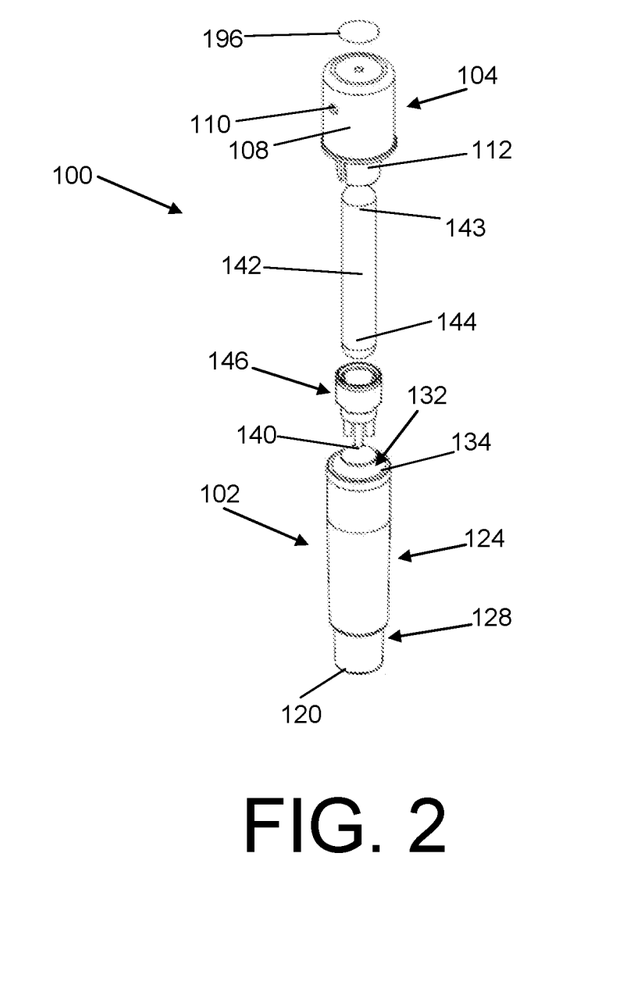
FIG. 2 depicts an isometric exploded view of the first SCBI example depicted in FIG. 1.
Figure 3:
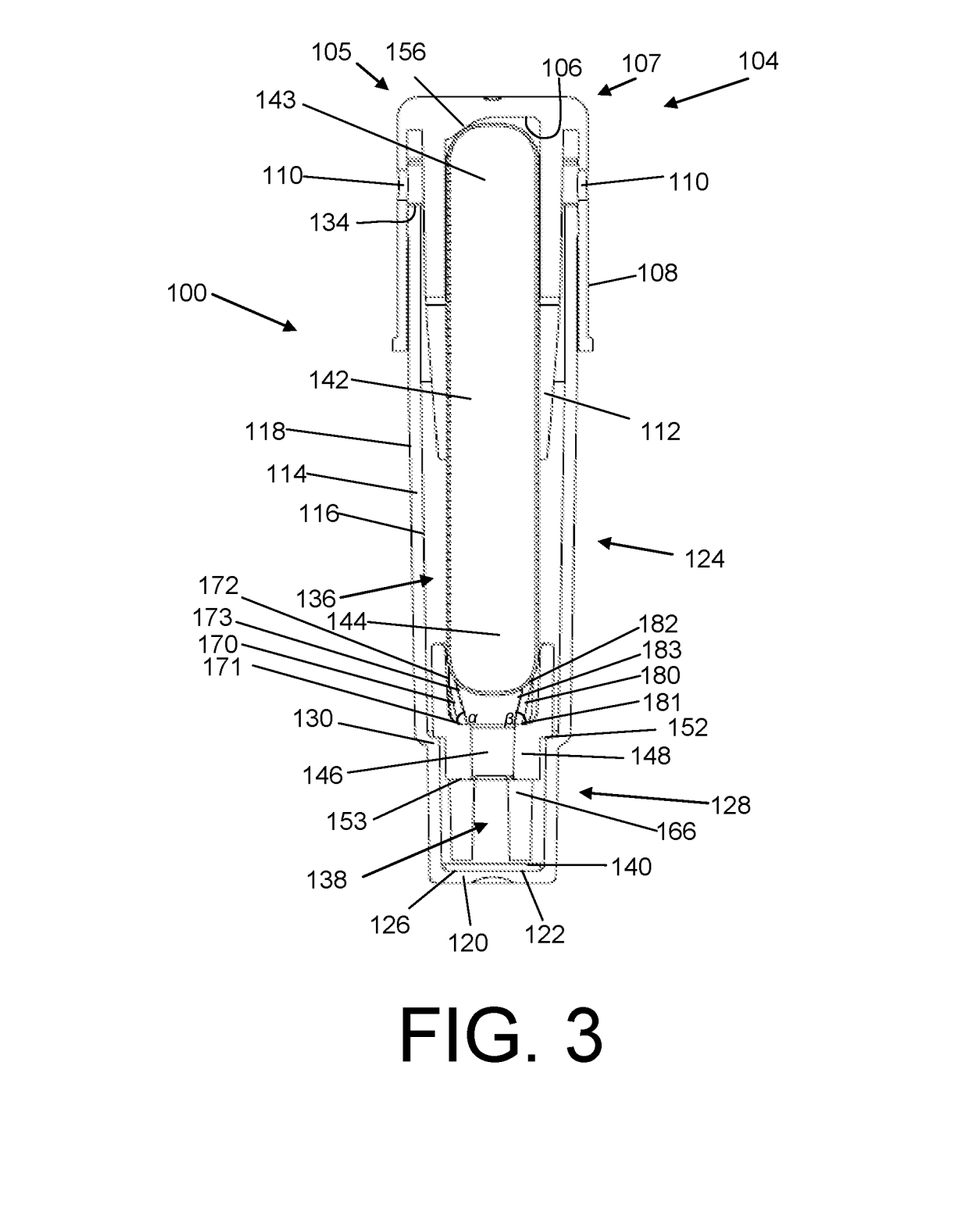
FIG. 3 depicts a cross-section of the first SCBI example depicted in FIGS. 1-2 taken along line A-A of FIG. 1.

Referring to FIGS. 1-3, a self-contained biological indicator ("SCBI") 100 is shown. SCBI 100 includes a housing 102 and a cap 104. Cap 104 includes an inner surface 106, an outer surface 108, and a projection 112 that has a planar, angled, arcuate, annular, or conical shape, or some combination thereof. Cap 104 may further include one or more through-holes 110, to assist in the passage of gasses (e.g., air or sterilant) into or out from the SCBI. A chemical indicator 196, which may be a sticker that changes color when exposed to a sterilant, may be affixed to the cap. Inner surface 106 may additionally include a curved portion 156. Housing 102 includes a side wall 114 having an inner side wall 116 and an outer side wall 118, a bottom wall 120 having an inner bottom wall 122 and an outer bottom wall 126. Housing 102 further includes a support 130 formed by a constriction of side wall 114. Top end 134 of housing 102 may define an aperture 132 therethrough, opposite bottom wall 120. Housing 102 may further be defined by a top portion 124 and a bottom portion 128 with support 130 disposed therebetween, further defining within housing 102 a first enclosure 136 and a second enclosure 138. Cap 104 is disposed relative to housing 102 in a first position and is configured to be movable from the first position to a second position, as is known in the art of SCBIs. In the first position (shown in FIGS. 1 and 3), Cap 104 is coupled to housing 102 in a manner in which gases (e.g., air or sterilant) may move from the surrounding environment and into the SCBI, or vice versa. In this position, any through-holes 110 in cap 104 are disposed above top end 134 such that first enclosure 136 and second enclosure 138 are in fluid communication with the surrounding environment, which permits introduction and withdrawal of sterilant into and from first enclosure 136 and second enclosure 138 via through-holes 110. Cap 104 may be depressed into a second position relative to housing 102. In this second position, through-holes 110 are disposed below top end 134 with cap 104 and outer side wall 118 in a tight-fitting relationship, which obstructs through-holes 110, effectively sealing the first enclosure 136 and second enclosure 138 from the surrounding environment.

SCBI 100 also includes a source of microorganisms or active enzymes, such as carrier 140, which is impregnated with bacterial spores, other forms of bacteria (e.g., vegetative), and/or active enzymes. Spores from Bacillus, Geobacillus, and Clostridia species are often used to monitor sterilization processes utilizing saturated steam, hydrogen peroxide, dry heat, gamma irradiation and ethylene oxide. Accordingly, carrier 140 may be impregnated with spores from Bacillus, Geobacillus, and/or Clostridia species. Carrier 140 may be water-absorbent and may be formed of filter paper. Sheet-like materials such as cloth, nonwoven polypropylene, rayon or nylon, and microporous polymeric materials may also be used. Non-water absorbent materials are also appropriate for use, such as metals (e.g., aluminum or stainless steel), glass (e.g., glass beads or glass fibers), porcelain, or plastic. Additionally, carrier 140 can be constructed of a combination of the aforementioned materials. In some embodiments, carrier 140 rests upon inner bottom wall 122. In some embodiments, carrier 140 may have a thickness of approximately 0.1 to 0.5 millimeters.

SCBI 100 also includes a frangible glass ampule 142, having a first end 143 and a second end 144. Ampule 142 may contain a liquid growth medium. The growth medium should be capable, with incubation, of promoting growth of any viable microorganisms disposed on carrier 140. In some embodiments, the growth medium does not promote growth of, e.g., contaminating microorganisms that were not purposefully disposed on carrier 140 because such contaminants could cause a color or fluorescence change, which could lead to incorrect determinations of sterilization efficacy. Ampule 142 may also include, either within or separate from the growth medium, a growth indicator. The growth indicator may be an enzyme or dye, e.g., a fluorescent dye, which aids in detecting growth of surviving microorganisms. The growth indicator may also be an enzyme substrate system, which may be a substance or mixture of substances that an enzyme may act upon and convert into an enzyme-modified product or products. For example, the enzyme substrate system may be a fluorogenic substrate that fluoresces differently than an enzyme-modified product produced by a reaction between an enzyme and the fluorogenic substrate. In some embodiments, the fluorogenic substrate fluoresces little if at all and the enzyme-modified product fluoresces significantly more than the substrate.

SCBI 100 may also include an insert 146, which is detailed in FIGS. 3-6. Insert 146 may include a platform 148 having a top surface 150, an abutment surface 152, a bottom surface 153, and one or more side surfaces, such as lower side surface 154, and upper side surface 155. Insert 146 may also include a tubular wall portion 164 on platform 148 that originates from top surface 150 and/or side surface 154 and extends away from abutment surface 152. Tubular wall portion 164 may have a hollow-cylindrical form. The diameter of this cylinder should be greater than the diameter of ampule 142 such that second end 144 may be disposed within tubular wall portion 164.

Figure 4:
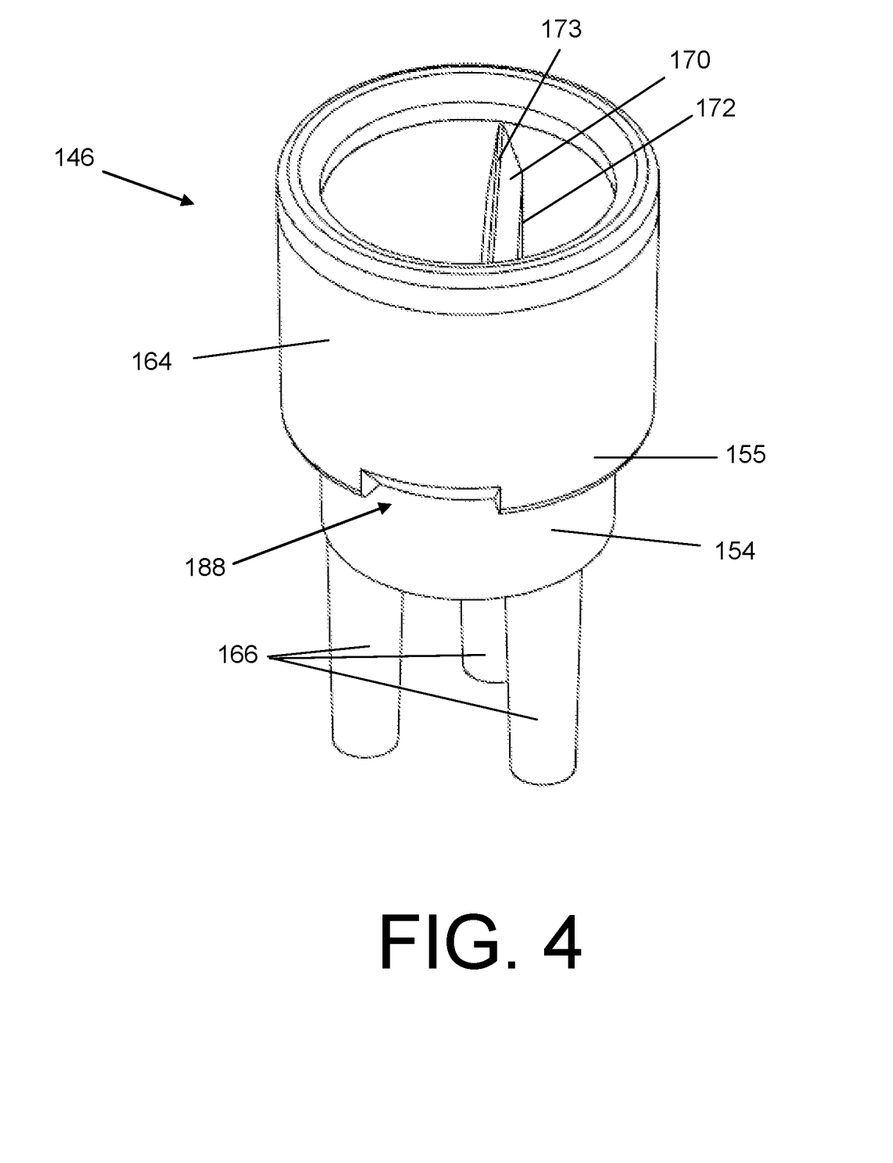
FIG. 4 depicts an isometric view of a first example embodiment of an insert of the first SCBI example depicted in FIGS. 1-3.
Figure 5:
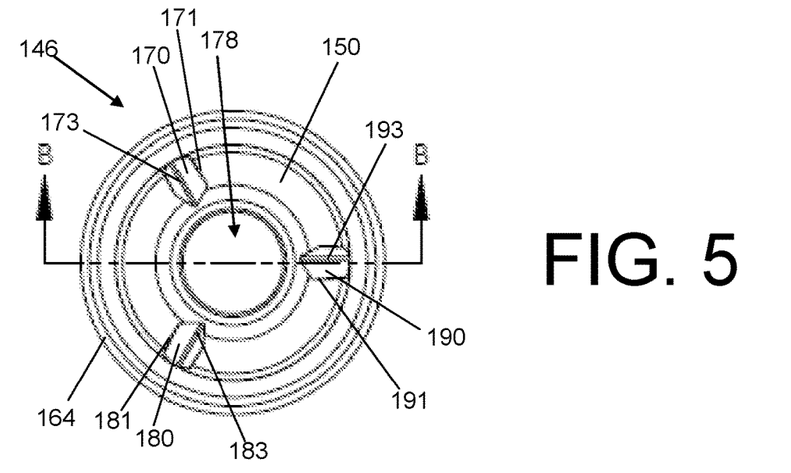
FIG. 5 depicts an top view of the first example embodiment of the insert of FIG. 4.
Figure 6:
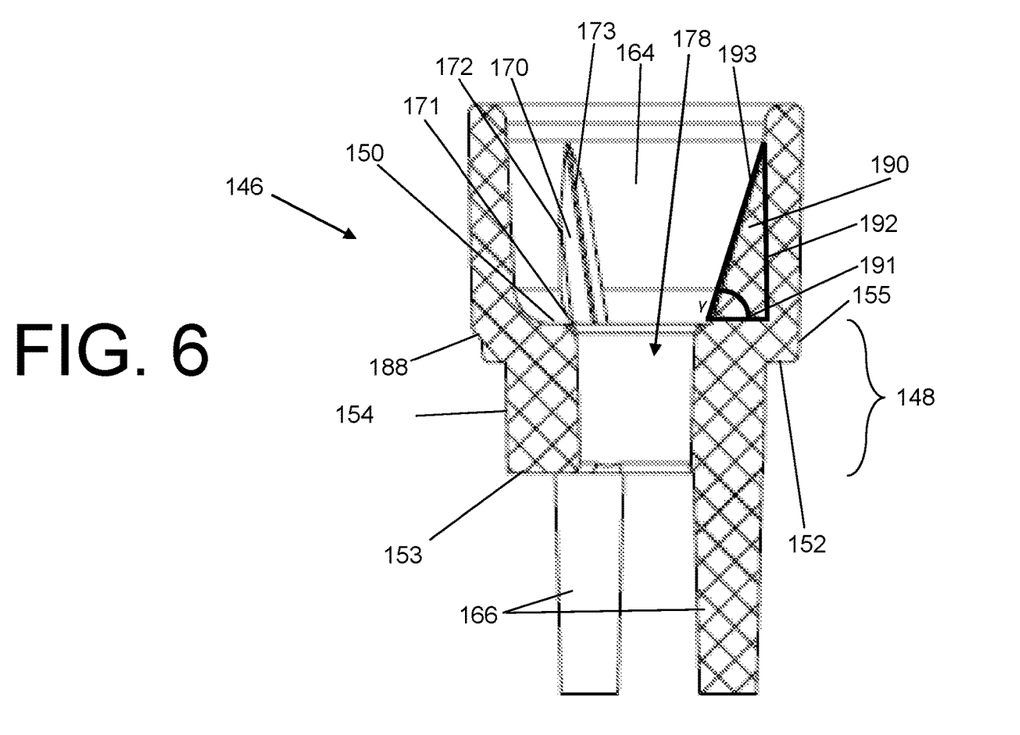
FIG. 6 depicts a cross section of the first example embodiment of the insert of FIGS. 4-5 taken along line B-B of FIG. 5.

A first void (or passage) 178, may be disposed through platform 148. First void 178 may have the form of a bore that originates in top surface 150 and terminates in bottom surface 153. A second void (or passage) 188, may additionally or alternatively be disposed through platform 148. Second void 188 may have the form of an angled cut (e.g., chamfer or bevel) that originates, at least partially, in side surface 154 and terminates, at least partially, in abutment surface 152. Although not shown, void 188 may additionally intersect top surface 150. Insert 146 may include additional instances of void 178 and void 188. For example, in some embodiments, three instances of void 188 are disposed through platform 148 from upper side surface 155 to abutment surface 152.

Insert 146 may also include a leg (or legs) 166 that originates from bottom surface 153 and extends away from platform 148. Leg 166 has a maximum length equal to the distance between support 130 and inner bottom wall 122 of housing 102. As shown in FIG. 3, leg 166 has a length that is somewhat less than the distance between support 130 and inner bottom wall 122 of housing 102. Leg 166 may have a length that is approximately 0.1 to 1 millimeter less than the distance between support 130 and inner bottom wall 122 of housing 102. Insert 146 may include multiple instances of leg 166. For example, insert 146 may include three instances of leg 166.

Insert 146 may also include a protrusion, or stress concentrator, 170 disposed upon top surface 150 of platform 148. Stress concentrator 170 may have the form of, e.g., a rounded bump, an angled bump, or a wedge, such as a triangular wedge. As shown in FIGS. 3-6, stress concentrator 170 has the form of a triangular wedge. The triangular wedge may have the form of a right triangle, including a base portion 171, a height portion 172, and a hypotenuse portion 173. Base portion 171 may be coincident with top surface 150 and height portion 172 may be coincident with upper side surface 155 and/or tubular wall portion 164. In such an embodiment, stress concentrator 170 may function as a gusset that may strengthen the junction of tubular wall portion 164 and platform 148. Base portion 171 may be disposed at a first angle $\alpha$ to hypotenuse portion 173. The first angle $\alpha$ may be acute. The first angle may have a value between 45° and 85°.

Insert 146 may additionally include multiple stress concentrators. For example, in addition to stress concentrator 170, it may also include a stress concentrator 180 and a stress concentrator 190. Like stress concentrator 170, stress concentrators 180 and 190 may also each have the form of, e.g., a rounded bump, an angled bump, or a wedge, such as a triangular wedge. As shown in FIGS. 3 and 5, stress concentrator 180 has a triangular form and includes a base portion 181, a height portion 182, and a hypotenuse portion 183. Stress concentrator 190 also has a triangular form that includes a base portion 191, a height portion 192, and a hypotenuse portion 193. Base portion 181 may be disposed at a second angle, $\beta$, to hypotenuse portion 183 and base portion 191 may be disposed at a third angle, $\gamma$, to hypotenuse portion 193. The second angle and the third angle may be acute. The second angle and the third angle may have a value between 45° and 85°. The second angle and third angle may be equal to each other and to the first angle. The second angle and third angle may be equal to each other but unequal to the first angle. The first angle, second angle, and third angle may each be unequal to each other. Insert 146 may be fabricated as an assembly of multiple components or may be manufactured as a single component, e.g., by injection molding.

Insert 146 is disposed within SCBI 100. Specifically, abutment surface 152 of platform 148 rests upon—or abuts—support 130. Accordingly, abutment surface 152 and support 130 together define a boundary between first enclosure 136 and second enclosure 138 of housing 102. Leg or legs 166 thus extend into second enclosure 138 and help maintain the position of carrier 140, which rests on inner bottom wall 122 and should remain there throughout the SCBI's life cycle. However, leg or legs 166 being shorter than the distance between support 130 and inner bottom wall 122, they do not contact inner bottom wall 122. Preferably, carrier 140 is sufficiently thin such that a clearance is also maintained between leg or legs 166 and carrier 140. Such clearance should help prevent damage to carrier 140 that otherwise could occur while the SCBI is being transported from a manufacturer's manufacturing facility to, e.g., a warehouse or a healthcare facility. Such transportation may be conducted by e.g., the manufacturer, an agent or employee of the manufacturer, or a common carrier (e.g., the United States Postal Service, the United Parcel Service). During transportation, which likely includes ground transportation, including by way of a ground-transportation vehicle such as a truck or a train, the SCBI may be subject to repeated jostling, caused by, e.g., bumps in roads or train tracks. This jostling could damage carrier 140 if leg or legs 166 were to contact carrier 140. In such instances, the jostling could, for example, cause leg or legs 166 to bounce repeatedly against carrier 140, which could cause carrier 140 to wear at any points of contact. In the worst case, the wear could be sufficient to create holes in carrier 140. Accordingly, to help prevent such damage, there should be approximately 0.1 to 0.4 millimeters of clearance between leg or legs 166 and carrier 140. Accordingly, following manufacture of SCBI 100, SCBI 100 may be loaded onto a standard shipping vehicle, such as a truck, and the vehicle may be driven to a destination, such as a healthcare facility or a warehouse, to transport SCBI 100 to the destination. Personnel at the destination may forego inspecting SCBI 100 for damage to carrier 140 based on the increased assurance that carrier 140 is not prone to damage during transportation. In an alternative embodiment, legs 166 may include thereon a retaining ledge, such as a ring that connects the legs, the ring having a diameter equal to or approximately equal to a diameter or a width of carrier 140. The retaining ledge may be spaced from carrier 140 by up to 0.4 mm. Alternatively, it may contact carrier 140 at an outer edge of carrier 140.

The position of glass ampule 142 is maintained within SCBI 100 by insert 146 and cap 104 in its first position such that ampule 142 does not contact housing 104. Curved portion 156 may assist in maintaining the position of ampule 142. As shown in FIGS. 1 and 3, a portion of ampule 142 is disposed within first enclosure 136 and a portion of ampule 142 is disposed above top end 134 of housing 102 but within cap 104. In first enclosure 136, second end 144 of glass ampule 142 rests against platform 148, or any one or more of stress concentrators 170, 180, and 190, such that second end 144 is disposed within tubular wall portion 164 of insert 146. Second end 144 of glass ampule 142 may contact stress concentrator 170 at a first point, stress concentrator 180 at a second point, and stress concentrator 190 at a third point. First end 143 of ampule 142 is disposed within cap 104. In some embodiments, first end 143 of ampule 142 may contact inner surface 106 of cap 104, and in some embodiments, curved portion 156, such that glass ampule 142 is constrained from vertical movement by its contacts with cap 104 and insert 146. In some embodiments, first end 143 of ampule 142 may also be disposed within projection 112.

Projection 112 may be configured to form a tight fit with ampule 142. Where projection 112 is of an annular form, projection 112 may have a diameter similar to or equal to the diameter of ampule 142. Accordingly, there may be a friction fit between ampule 142 and projection 112. Alternatively, the diameter of projection 112 may be slightly larger than the diameter of ampule 142 to provide between approximately 0.1 mm and 3 mm of clearance between the ampule 142 and the projection 112.

By constraining the position of ends 143 and 144 of ampule 142, the overall position of ampule 142 may be maintained within SCBI 100 until the time a user desires to use the SCBI, which may help prevent premature breakage of glass ampule 142, particularly during transportation from a manufacturing facility to another site, such as a healthcare facility.

In use, SCBI 100 is subjected to a sterilization cycle, preferably alongside medical devices being sterilized by the sterilization cycle. Following the sterilization cycle, a user activates SCBI 100 by applying force to cap 104, either using his or her hand or other body part, and/or with the assistance of a device adapted to aid the user in applying force to cap 104. Cap 104, and in some embodiments, curved portion 156, applies at least some of the force the user exerted on cap 104 to ampule 142, which generates a reaction force between cap 104 and top end 143. Ampule 142, via bottom end 144, applies at least some of the force the user applied to cap 104 to stress concentrators 170, 180, and 190 of insert 146, which in turn generates a reaction force between bottom end 143 and stress concentrators 170, 180, and 190 of insert 146. Insert 146, via support 130, applies at least some of the force the user applied to cap 104 to abutment surface 152, which generates a reaction force between abutment surface 152 and support 130. Ampule 142, being fabricated from glass, fractures into glass shards when the force applied by the user to cap 104 generates stresses within ampule 142 that are greater than ampule 142 can withstand. Stress concentrators 170, 180, and 190 aid in increasing the stress within ampule 142 for a given force that the user applies directly to cap 104 and indirectly to ampule 142 because the surface area of the points of contact between bottom end 144 of ampule 142 and stress concentrators 170, 180, and 190 is less than the surface area of cap 104 to which a user applies force to activate the SCBI and/or less than the surface area of the points of contact between cap 104, which may include curved portion 156, and top end 143 of ampule 142.

Once fractured, ampule 142 is no longer present to resist the force applied by the user to the cap. Accordingly, the force applied by the user causes cap 104 to move to a second position in which the cap effectively seals SCBI 100. Insert 146 prevents the glass shards from entering second enclosure 138 such that some glass shards settle on platform 148 and the remaining glass shards settle on top of other glass shards.

The fracturing of ampule 142 also releases some volumes of the liquid growth medium to flow downward through the shards and through void 178, ultimately collecting in second enclosure 138. Other volumes of the liquid growth medium are projected toward inner side wall 116 of housing 102. Some of these volumes impinge upon inner side wall 116 and then flow downward to pass through space between inner side wall 116 and insert 146, ultimately collecting in second enclosure 138.

Voids 178 and 188 provide openings through which fluids such as the growth medium, gases (e.g., air), vapors, and sterilant may flow. These openings function as passages that help maintain fluid communication within housing 102 between first enclosure 136 and second enclosure 138. Specifically, void 178 helps maintain fluid communication through insert 146 and void 188 helps maintain fluid communication along the side of insert 146, between wall 164 and inner side wall 116 of housing 102.

Voids 178 and 188 may further facilitate the flow of liquid growth medium into second enclosure 138 by way of reducing the impedance to the downward flow of the liquid growth medium otherwise caused by the glass shards, platform 148, and the gas within second enclosure 138 that must be displaced for the liquid growth medium to enter. Voids 178 and 188 reduce the likelihood that gas within second enclosure 138 may become trapped by volumes of the liquid growth medium that pool, e.g., between pieces of glass shards, which could prevent displacement of the gas within second enclosure 138 and, correspondingly, prevent the full volume of the liquid growth medium from entering second enclosure 138. This mechanism, referred to herein as a "liquid lock," could result in maintaining a volume of the liquid growth medium in the first enclosure, away from carrier 140, which could prevent a successful culture of any microorganisms on carrier 140 that may have survived the sterilization cycle, which could in turn increase the likelihood of an erroneous determination of the cycle's efficacy.

The likelihood of a liquid lock forming is further reduced, or inhibited, by allowing volumes of liquid the growth medium to impinge, largely unobstructed, upon inner side wall 116 above support 130 because the surface area of inner side wall 116 that the liquid may initially wet is maximized, which allows a greater volume of the liquid to flow downward along inner side wall 116, instead of through the concentration of glass shards that collect upon insert 146. By reducing the volume of the liquid that flows over and through the concentration of shards, the likelihood that liquid may pool between pieces of the shards and form a liquid lock is minimized.

As noted, after ampule 142 is broken, glass shards that were once ampule 142 collect upon platform 148 of insert 146 to remain in first enclosure 136, while the liquid growth medium collects in second enclosure 138. At this point, the user incubates SCBI 100 using an incubator device as is known in the art to encourage outgrowth of surviving microorganisms. Following incubation, the liquid growth medium in second enclosure 138 may be assayed to determine whether any microorganisms may have survived the sterilization cycle. Because second enclosure 138 does not include glass shards within the liquid growth medium, the glass shards do not foul the accuracy of any readings taken visually or by color or fluorescence sensors. Accordingly, the reliability of a determination of the efficacy of the sterilization cycle is improved over a similar determination based on an assay of a mixture of liquid growth medium and glass shards.

II. Structures that Facilitate Ampule Breakage

A user applies force to cap 104 in order to activate SCBI 100 and break glass ampule 142. The amount of force the user must apply to cap 104 may be minimized by providing structures within SCBI 100 that concentrate the user-applied force onto small areas of glass ampule 142 as compared to distributing the resistive force over larger areas of glass ampule 142. Referring to FIGS. 1-4, insert 146 includes stress concentrators 170, 180, and 190. Glass ampule 142 rests upon these stress concentrators. Specifically, second end 144 of glass ampule 142 contacts stress concentrator 170 at a first point, stress concentrator 180 at a second point, and stress concentrator 190 at a third point. Accordingly, force applied to cap 104 causes reaction pressure to be concentrated at these three points. Because pressure equals force divided by surface area (P=F/A), for a given force, pressure is inversely proportional to surface area. Thus, reactive pressure is maximized by minimizing the surface area that resists the force that cap 104 applies to ampule 142. The three points thus maximize the reactive pressure against the glass ampule. Although, in theory, one or two points may result in a greater reactive pressure, in some embodiments three points of contact may be used in order to maintain the position of ampule 142 as described above.

As noted, stress concentrators 170, 180, and 190 need not be identical. For example, although they may each have a triangular form, the angle between their respective base portions (171, 181, 191) and hypotenuse portions (173, 183, 193) may differ somewhat. When these angles differ, the resistive forces applied by stress concentrators 170, 180, and 190 to ampule 142 are applied asymmetrically. It is believed that this asymmetric application of force causes an increase in the stress generated in ampule 142, thereby reducing the amount of force the user must apply to cap 104 in order to break ampule 142.

A further asymmetry between the forces may be achieved in those embodiments where inner surface 106 of cap 104 contacts ampule 142 in an asymmetric manner. For example, as seen in FIG. 3, curved portion 156 contacts first end 143 on the left side 105 of first end 143, but not on the right side 107 of first end 143. Accordingly, a downward force applied by the user to cap 104 results in cap 104 imparting a force to ampule 142 that includes a lateral component.

In embodiments employing stress concentrators 170, 180, and 190, ampule 142 may be broken following the application of an applied force to cap 104 that generates at least four resistive forces at discrete locations upon ampule 142. These resistive forces occur at least where ampule 142 contacts: (1) inner surface 106 of cap 104, which in some embodiments includes curved portion 156, (2) stress concentrator 170, (3) stress concentrator 180, and (4) stress concentrator 190.

Figure 7:
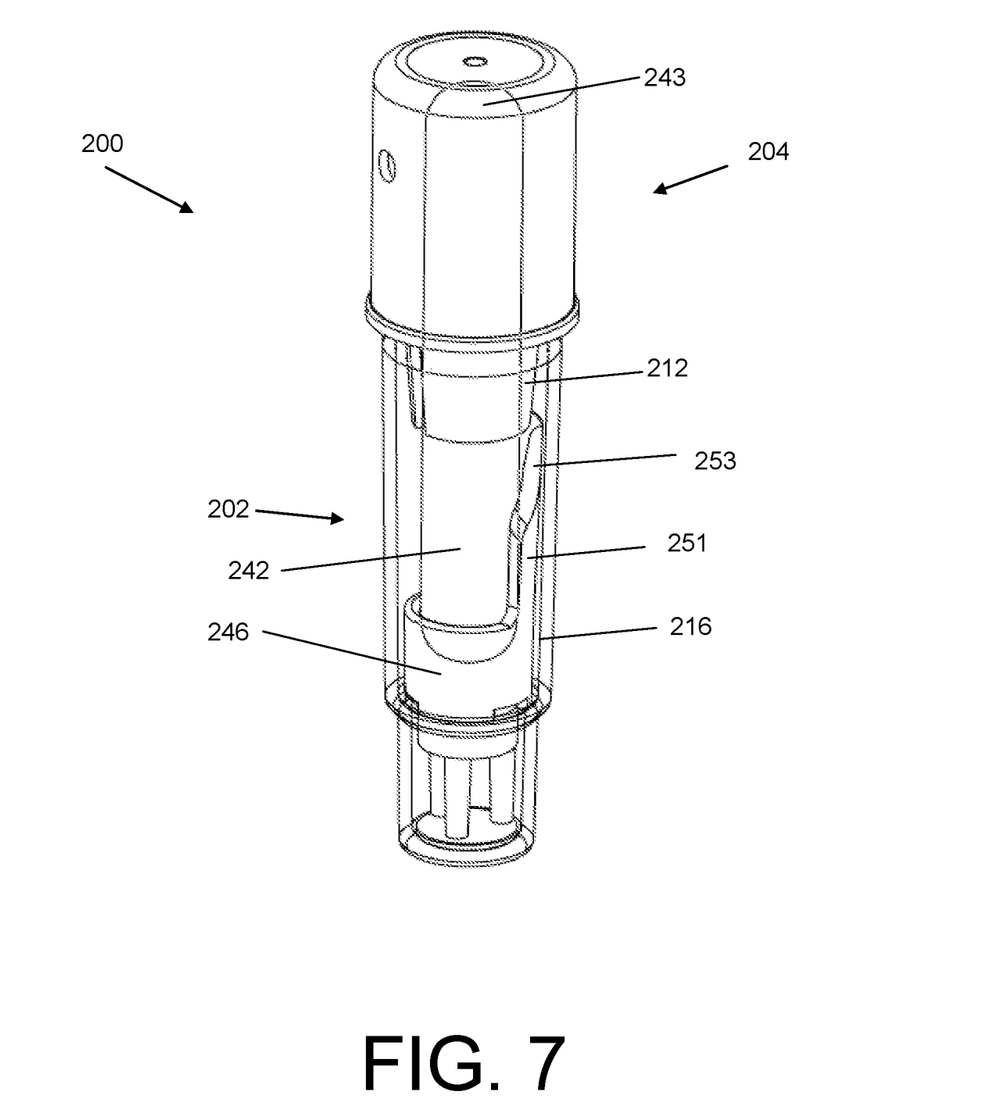
FIG. 7 depicts an isometric view of a second example embodiment of an SCBI.
Figure 8:
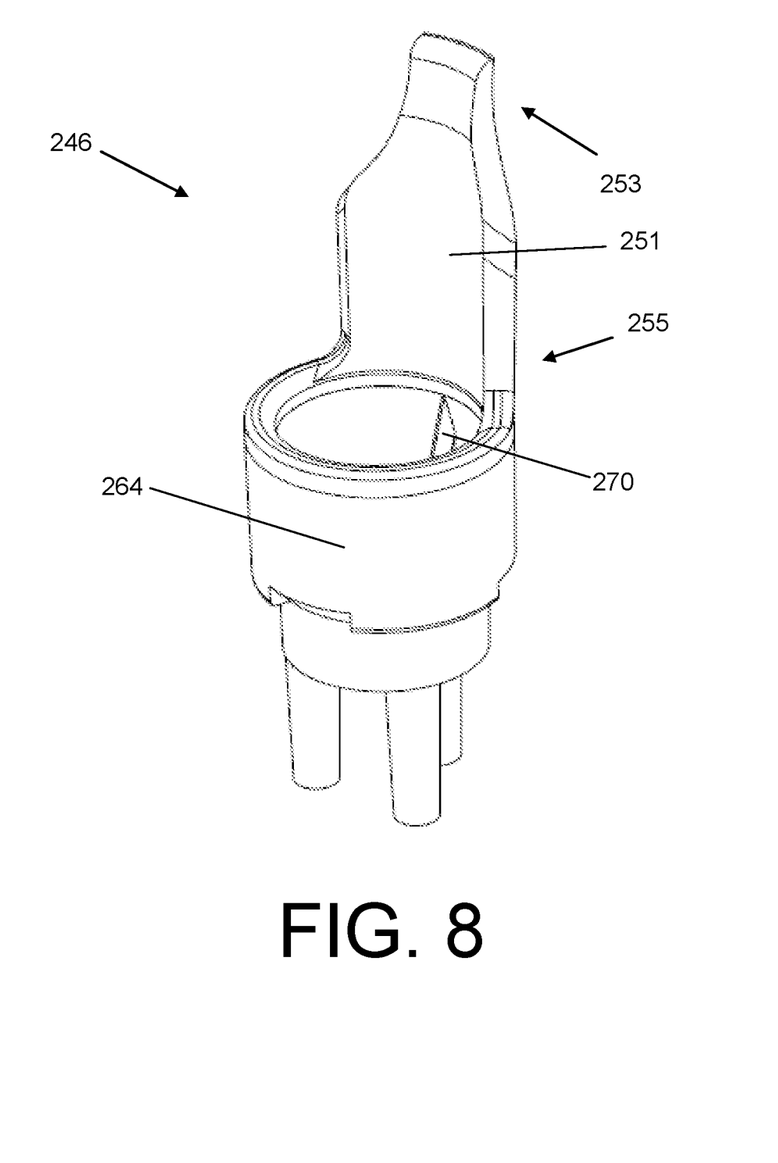
FIG. 8 depicts an isometric view of a second example embodiment of an insert of the second SCBI example depicted in FIG. 7.

Referring to FIGS. 7-8, another embodiment of the technology is shown. SCBI 200 includes insert 246, a housing 202, and a cap 204. Insert 246 includes a tubular wall portion 264. Originating from tubular wall portion 264 is an arm (or finger) 251. Arm 251 has a top portion 253 and a bottom portion 255. Bottom portion 255 is disposed upon and connected to tubular wall portion 264. Arm 251 is fabricated from a semi-rigid material, such as plastic, and has a thickness such that arm 251 may flex when subject to compressive and/or lateral force. For example, when a lateral force is applied to top portion 253, arm 251 may laterally flex about bottom portion 255 where arm 251 connects to tubular wall portion 264. Arm 251 may be hollow or have one or more channels or apertures disposed therein to reduce the amount of force required to cause arm 251 to deflect. The channels or apertures may also help prevent arm 251 from blocking the liquid growth medium from impinging on inner side wall 216 when ampule 242 is broken, which is important for minimizing the likelihood of a liquid lock, as explained above with respect to SCBI 100. Insert 246 may be fabricated as an assembly of multiple components or may be manufactured as a single component, e.g., by injection molding.

Cap 204 includes a projection 212 that has a planar, angled, arcuate, annular, or conical shape, or some combination thereof. As shown in FIG. 7, arm 251 is configured in a manner whereby top portion 253 of arm 251 is disposed in proximity of projection 212. In some embodiments, top portion 253 may contact projection 212. In other embodiments, there may be approximately 0.1 mm to 5 mm of lateral and/or vertical clearance between top portion 253 and projection 212.

SCBI 200 functions similarly to SCBI 100, but less force may be applied to cap 204 of SCBI 200 in order to break glass ampule 242 than may be applied to cap 104 of SCBI 100 in order to break glass ampule 142 because of arm 251. In use, when a user applies force to cap 204, arm 251 impedes movement of cap 204 by way of interference because arm 251 is an obstruction in the path of projection 212. Arm 251 is not a complete obstruction, however, because it may flex about its connection to tubular wall portion 264 toward inner side wall 216 from a first orientation to a second orientation. In some configurations, the flexion of arm 251 is limited by inner side wall 216. As cap 204 is depressed by application of an applied force thereto, a lateral force caused by arm 251 impeding the motion of projection 212 acts on projection 212, causing projection 212 to flex or pivot from a third orientation to a fourth orientation. Accordingly, projection 212 applies a lateral reaction force to glass ampule 242. In so doing, glass ampule 242 impedes the movement of cap 204 and projection 212, and any reaction forces generated at points where ampule 242 contacts other components of the SCBI are exerted asymmetrically upon ampule 242 until the stresses within ampule 242 become sufficiently large to break it. As with insert 146, insert 246 may include multiple stress concentrators. For example, a first stress concentrator 270 is visible in FIG. 8. In some embodiments of insert 246, three stress concentrators may be employed, similar to insert 146. It is believed that this asymmetric application of force causes an increase in the stress generated in ampule 242, thereby reducing the amount of force the user must apply to cap 204 in order to break ampule 242.

In embodiments employing first stress concentrator 270, a second stress concentrator, a third stress concentrator, and arm 251, ampule 242 may be broken following the application of an applied force to cap 204 that generates at least five reaction forces at discrete locations upon ampule 242. These reaction forces occur at least where (1) top portion 243 of ampule 242 contacts cap 204, (2) ampule 242 contacts first stress concentrator 270, (3) ampule 242 contacts the second stress concentrator, (4) ampule 242 contacts the third stress concentrator, and (5) arm 251 deflects stress concentrator 212 into ampule 242.

The relative positions of arm 251 and projection 212 may be reversed such that projection 212 is closer to inner side wall 216 than arm 251 and such that arm 251 contacts ampule 242 to help maintain its position within housing 202. In this configuration, when cap 204 is depressed, projection 212 applies a lateral force to arm 251, which in turn applies a lateral force to glass ampule 242.

It should be understood that any of the examples and/or embodiments described herein may include various other features in addition to or in lieu of those described above. The teachings, expressions, embodiments, examples, etc. described herein should not be viewed in isolation relative to each other. Various suitable ways in which the teachings herein may be combined should be readily apparent to those of ordinary skill in the art in view of the teachings herein.

Having shown and described exemplary embodiments of the subject matter contained herein, further adaptations of the methods and systems described herein may be accomplished by appropriate modifications without departing from the scope of the claims. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

I claim:

1. A method of using a biological sterilization indicator comprising:
   (a) providing the biological sterilization indicator, the biological sterilization indicator comprising
   (i) a housing having a first enclosure and a second enclosure,
   (ii) an ampule containing a liquid growth medium, wherein the ampule is disposed within the housing, and
   (iii) an insert disposed at least partially inside the first enclosure, the insert having
   a platform including a top surface, an abutment surface, and a side surface,
   a first void disposed through the platform and configured to allow passage of a first volume of the liquid growth medium into the second enclosure, and
   a second void being angled cut through at least a portion of the side surface and a portion the abutment surface, and configured to allow passage of a second volume of the liquid growth medium into the second enclosure, the second void being an enclosed opening enclosed by the portion of the side surface and the portion of the abutment surface, and the abutment surface abuts a portion of the housing;
   (b) breaking the ampule;
   (c) allowing passage of the first volume of the liquid growth medium through the first void; and
   (d) allowing passage of the second volume of the liquid growth medium through the second void.

2. The method of claim 1 further comprising inhibiting a liquid lock from forming.

3. The method of claim 1, wherein the angled cut is disposed entirely beneath the top surface.

4. The method of claim 3, wherein the insert further includes a wall disposed on the top surface of the platform.

5. The method of claim 4, wherein the wall has a cylindrical form.

6. The method of claim 1, wherein at least a portion of the ampule is disposed inside the first enclosure.

7. The method of claim 1, wherein the insert includes a leg.

8. The method of claim 7, wherein the biological sterilization indicator includes a cap having an inner surface and an outer surface, the cap disposed on a portion of the first enclosure.

* * * * *